United States Patent
Stern et al.

(10) Patent No.: US 6,214,335 B1
(45) Date of Patent: Apr. 10, 2001

(54) LIVESTOCK MUCOSAL COMPETITIVE EXCLUSION CULTURE TO REDUCE ENTEROPATHOGENIC BACTERIA

(75) Inventors: Norman J. Stern; Nelson A. Cox; J. Stan Bailey, all of Athens, GA (US); Paula J. Cray, Ames, IA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/105,306

(22) Filed: Jun. 26, 1998

Related U.S. Application Data

(62) Division of application No. 08/729,113, filed on Oct. 11, 1996, now Pat. No. 5,807,546.

(51) Int. Cl.[7] ........................................ C12N 1/20
(52) U.S. Cl. .................. 424/93.3; 424/93.4; 424/93.45
(58) Field of Search ................... 424/93.3, 93.45, 424/93.4

(56) References Cited

U.S. PATENT DOCUMENTS

| | | | |
|---|---|---|---|
| 4,335,107 | 6/1982 | Snoeyenbos et al. | 424/93.3 |
| 4,657,762 | 4/1987 | Mikkola et al. | 424/93.3 |
| 5,401,501 | 3/1995 | Pratt | 424/93.45 |
| 5,451,400 | 9/1995 | Stern et al. | 424/93.3 |
| 5,478,557 | 12/1995 | Nisbet et al. | 424/93.21 |

OTHER PUBLICATIONS

Asplund et al., "Note: Inhibition of the growth of *Yersinia enterocolitica* 0:3 by the microflora of porcine caecum and ileum in an in vitro model", *J. Appl. Bact.*, vol. 81, pp. 217–222 (1996).

Nurmi et al., "New Aspects of *Salmonella* Infection in Broiler Production", *Nature*, vol. 241, pp. 210–211 (1973).

Freter, Rolf, "Factors affecting the microecology of the gut", in *Probiotics: The Scientific Factor*, by Roy Fuller, Chapman & Hall, published Jun. 1992, pp. 111–144.

Tarakanov, *Sel–skokhozyaistvennaya Biologiya*, vol. 0(6), pp. 119–128(1985).

Sanni et al., *Chemie Mikrobiologi Technologie der Lebensmittel*, vol. 17(3–4), pp. 99–104(1995).

Abe et al., *Journal of Dairy Science*, vol. 78(12), pp. 2838–2846(1995).

*Primary Examiner*—Jean C. Witz
(74) *Attorney, Agent, or Firm*—M. Howard Silverstein; John D. Fado; Gail E. Poulos

(57) ABSTRACT

A preparation from the scrapings of healthy animals is cultured and administered to animals. This preparation confers a strong measure of protection against the subsequent colonization by enteropathogenic bacteria, including Salmonella species, Campylobacter species and *Escherichia coli* 0157:H7, which currently cause an unacceptably high incidence of morbidity and mortality in humans and reduce productivity in livestock populations.

6 Claims, No Drawings

LIVESTOCK MUCOSAL COMPETITIVE EXCLUSION CULTURE TO REDUCE ENTEROPATHOGENIC BACTERIA

This is a division of application Ser. No. 08/729,113 filed Oct. 11, 1996, now U.S. Pat. No. 5,807,546, which is herein incorporated by reference in its entirety.

BACKGROUND OF THE INVENTION

1. Field of the Invention

This invention relates to a bacterial culture prepared from the intestinal tract of pathogen-free mammalian animals. It also relates to subcultures of such cultures and to methods of using the subcultures to protect livestock from colonization by enteropathogenic bacteria.

2. Description of the Related Art

Enteropathogens, such as Salmonella and *Escherichia coli* 0157:H7, cause an unacceptably high incidence of morbidity and mortality in humans and may reduce productivity in livestock populations. Gastrointestinal pathogens in humans are typically derived from intestinal contamination of meats that humans consume. At a symposium on *Tracking Foodborne Pathogens from Farm to Table: Data Needs to Evaluate Control Groups* held in January, 1995, a question asked was "How important are foodborne diseases?" (Tracking Foodborne Pathogens from Farm to Table: Data Needs to Evaluate Control Groups, Washington, D.C., 3–29, 1995). It was stated that in the United States, there are an estimated 6.5 million to 33 million cases of foodborne diseases each year, resulting in up to 9,000 deaths. The USDA Economic Research Service estimates U.S. medical costs and productivity losses for seven foodborne pathogens at $5.6 billion to $9.4 billion annually. Menning estimates that there are over 5 million cases of meat and poultry foodborne diseases in the United States per year and a large percentage is attributable to Salmonella and Campylobacter infections (*J. Am. Vet. Med. Assoc.*, Volume 192, 494–497, 1988). Roberts estimates that each case of salmonellosis costs $700 (*Amer. J. Agr. Econ.*, Volume 71, 468–474, 1989). Based on surveys estimating foodborne disease in other countries, it would not be unreasonable to project that the number of worldwide foodborne diarrheas per year attributable to Salmonella probably exceeds 100 billion with an estimated cost exceeding 25 billion dollars. These pathogens also account for pain, suffering and loss of life. In addition, enteropathogenic bacteria may also cause substantial economic loss through infection of livestock.

Competitive exclusion (CE) techniques are used for decreasing colonization of enteropathogenic bacteria in poultry. Nurmi et al (*Nature*, Volume 241, 210–211 1973) found that preparations from mature, healthy chickens conferred protection to young chicks, whose microflora had not yet been established, against Salmonella colonization. Administration of undefined CE preparations to chicks speeds the maturation of gut flora in newly-hatched birds and provides a substrate for the natural process of transmission of microflora from the adult hen to its offspring.

Snoeyenbos et al (U.S. Pat. No. 4,335,107, June, 1982) developed a CE micorflora technique for preventing Salmonella colonization by lyophilizing fecal droppings and culturing this preparation anaerobically. Mikola et al (U.S. Pat. No. 4,657,762, April, 1987) used intestinal fecal and cecal contents as a source of CE microflora for preventing Salmonella colonization. Treatment with this type of culture required media to be anaerobic and pH balanced.

Stern et al (U.S. Pat. No. 5,451,400, Sep. 19, 1995) discloses a mucosal CE composition for protection of poultry against colonization by Salmonella and Campylobactor where the mucin layer of prewashed ceca is scraped and the scrapings, kept in an oxygen-free environment, are cultured anaerobically.

Nisbet et al (U.S. Pat. No. 5,478,557; Dec. 26, 1996) disclose a probiotic that can be obtained from a variety of domestic animals, including but not limited to fowl and also equine, porcine and bovine. Nisbet et al disclose that a stable defined probiotic is preferably obtained by continuous culture of a batch culture produced directly from fecal droppings, cecal and/or large intestine contents of the adult target animal. They further disclose that large quantities of the probiotic may be produced by either batch or continuous culture wherein the batch culture is continued until the concentration of acetic acid is greater than or equal to about 20 mM, the concentration of proprionic acid is greater than or equal to about 10 mM and the concentration of butyric plus isobutyric acid is greater than or equal to 15 mM.

Asplund et al (*Journal of Applied Bacteriology*, Volume 81, 217–223, 1996) report an in vitro model of the procine intestine and its use to show inhibiiton of *Yersinia enterocolitica* O:3 by pig ileal and caecal microflora. Caeca and distil parts of the small intestine are collected, kept under anaerobic conditions and the contents collected, pooled and cultivated. Caecal and ileal inocula are shown to suppress the growth of cultured *Y. enterolitica*, with caecal flora somewhat more effective than ileal flora. No in vivo efficacy was reported.

The present invention provides for the first time a composition and a method for reducing in vivo and/or preventing colonization of mammals, especially livestock, by enteropathogenic bacteria.

SUMMARY OF THE INVENTION

It is therefore an object of the present invention to provide an animal mucosal derived subculture for the control of enteropathogenic bacteria colonization of animals.

It is another object of the present invention to provide a method for treating animals to control enteropathogenic bacterial colonization of animals by using a preparation derived from a mucosal culture.

Further objects and advantages will become apparent from the following description.

DETAILED DESCRIPTION OF THE INVENTION

The importance of enteric infections in humans has been increasingly well recognized over the last dozen years. The relationship of livestock contamination and human infection has, likewise, become well documented. During production and processing of animals, such as livestock, fecal material containing pathogens may be transferred onto meat and persist into food processing kitchens. Swine, along with poultry, cattle and seafood, are important carriers of Salmonella (Bean et al, *J. Food Protect.*, Volume 53, 804–817, 1990; Lammerding et al *J. Food Protect.*, Volume 51, 47–52, 1988). Naive animals are infected from contaminated feed, chronic carriers which are introduced into the population, infected rodents, or from contaminated farm personnel (Heard, *Vet. Rec.*, Volume 85, 482–484, 1969; Williams et at, *J. Hyg. Camb.*, Volume 66, 281–293, 1968; Wilcock et al, *Diseases in Swine*, Leman et al, eds., Iowa State University Press, Ames, Iowa, 570–583, 1992; Duhamel et al, Proc. 12th Int. Symp. New and Emerging Infect. Dis., San Diego, Calif., 381, 1992). For swine, at the abattoir, the initial source of contamination is the carrier pig, and transmission is thought to occur by pig-to-pig contact or from exposure to the contaminated physical environment (Newell et al, *J. Am. Vet. Med. Assoc.*, Volume 158, 89–98, 1971). These infected animals, in turn, contaminate the premises, equipment, and personnel leading to contamination of the final product (Williams et al, Am. *J. Pub. Health*, Volume 60, 926–929, 1970; Newel et al, supra; Morgan et al, *Epidemiol. Infect.*, Volume 98, 323–330, 1987). The initial source, however, remains the carrier pig. Current efforts to identify and eradicate the carrier population in livestock has been impeded by a lack of information regarding the epidemiology and pathogenesis of salmonellosis in livestock. Because Salmonella species are widely distributed and persist well in the environment, elimination and control has been difficult. There is substantial amount of information regarding the virulence of Salmonella relevant to the pathogenesis in man. However, very little information is available regarding animal sources of this infectious agent. An understanding of the infectious process in food producing animal sources has assumed greater priority and control and elimination of the carrier animal will prevent zoonotic transmission of the disease. The control of food-borne disease can be best obtained through identification and eradication of the carrier population. While the carrier state may occur at any time throughout the animal's lifespan, exposure at birth will be the first opportunity for the animal to be exposed to the pathogen. The application of a mucosal culture for the control of pathogen colonization in food producing animals has been discovered. The term control means the reduction or prevention of enteropathogenic bacteria colonization. The term food-producing animals means any animal consumed by humans.

A unique bacterial culture is obtained from the scrapings of the intestinal tract of pathogen-free animals. The animals may be of any age, most preferred is the use of young animals, to protect newborn and older animals. This initial culture is subcultured and then administered to young animals. The method of this invention is applicable to any animal whether domesticated or wild and particularly to livestock raised for human consumption which could serve as a carrier for target pathogens. Livestock includes cattle, calves, hogs, pigs, sheep, lambs, buffalo, goats, rabbits, seafood and the like. It is preferred to administer the livestock mucosal competitive exclusion subculture (LMCES) preparation twice within the first 24 hours post partum. However, the preparation could be administered at any time during the life of the animal such as on a continual basis or at selected times throughout the life span of the animal, for example. The term "continual basis" means a consistent source of LMCES is provided by administration through drinking water, feeds, by oral gavage or aerosolization. The LMCES can be administered daily in feed or water, weekly, monthly, etc. for the continual basis. The term "at selected times throughout the life span of the animal" means administration of the LCME culture at critical control points, such as occurs during birth, weaning, disease, antibiotic administration, excessive heat, dehydration, cold, during transport such as movement to other buildings in the production process and prior to transport at slaughter, etc.

The target pathogens include all human enteropathogenic bacteria capable of colonizing animals, especially livestock raised for human consumption. As used herein, "human enteropathogenic bacteria" are bacteria capable of or known to colonize the human alimentary canal or disseminating toxins therein, and which are capable of causing intestinal illness in a human host. Examples of human enteropathogenic bacteria include but are not limited to Salmonella species, Campylobacter species and *Escherichia coli*.

The LMCES can be combined with other cultures or treatments effective for the control of Salmonella in animals, such as for example, Lactobacillus, fructooligosaccharides and yeasts. Other conventional or known treatments of animals, and particularly for the inhibition of enteropathogens, may be added to the LMCES as long as they do not affect the activity of the LMCES preparation.

In methods of the present invention, compositions of livestock mucosal competitive exclusion subcultures (LMCES) are administered to animals. As used herein, "administering" includes any suitable method for orally delivering the compositions to animals as is known in the art, such as for example by oral gavage, feeding, spraying or applying a paste onto mothers teats or artificial teats, through administered milk etc. The LMCES may also be administered through the lower intestinal opening. The preparation can be in any form known in the art such as for example, liquid, paste, gel cap or aerosol form for administration. The LMCES preparations are administered to animals at any age including new born animals in amounts effective to at least reduce human enteropathogenic bacteria found in the gut of the animals. As used herein, 'a reduction of bacteria' or 'at least reduce human enteropathogenic bacteria' refers to a reduction in numbers of bacteria compared to that which would be expected in an animal which did not receive treatment according to the methods of the present invention. Any accurate method of measuring, counting and comparing bacteria present in the intestinal tract of animals may be used for such comparisons, as would be apparent to those skilled in the art. As used herein, "in amounts effective", "an effective amount", or "an amount effective", refer to the amount of LMCES preparation administered, wherein the effect of the administration acts to at least reduce human enteropathogenic bacteria found in all ages of animals. The amount of preparation will vary depending on the size of the animal being treated and the method of administration. For small animals, including small new born animals, about 4–8 mls of the second or later passaged 48 hour subculture passage LMCES culture can be administered by oral gavage, with about 5 ml being the preferred dose. For large animals, including large new born animals, the second 48 hour subculture passage or later of the LMCES can be undiluted or up to about 10 times diluted for oral administration in a liquid suspension where the diluent can be, for example, milk, water, etc. Additional subculture passages may also be employed but, will likely be less effective. Diluted and undiluted liquid LMCES preparations can be directly administered. For new born animals, the LMCES preparation is given within approximately 2–48 hours of birth, with approximately 2–6 hours from birth more preferred, followed by a second dose approximately 18–24 hours later. The most preferred treatment schedule is the first dose within about 6 hours of birth followed by the second dose about 24 hours after birth. In general, the first dose of treatment is given about 2 to 48 hours prior to weaning, transport, or movement to other buildings, with a preferred time of about 2–6 hours. In these instances, only one treatment may be required but a second treatment may be administered 18–24 hours after the first treatment. Variations in treatment schedules will reflect commercial husbandry practices. Additional doses may be given at weaning, prior to movement throughout a production facility or prior to transport at slaughter. If given in feed or water, daily administration would occur.

The LMCES preparation is prepared by aseptically removing the lower intestine including cecum of an animal and placing it in a sterile container. As used herein, lower intestine is defined the portion originating at the end of the stomach through to and including the cecum. This container is kept in an anaerobic environment throughout the preparation of the cultures. The selected length of the intestine is inverted by any means known in the art. The contents of the intestine are removed by a combination of washing and scraping. The washing is done with an appropriate anaerobic medium. The washing step may utilize any medium effective for the stated purpose, including water. A preferred medium is an anaerobic medium, particularly preferred being a pre-reduced, Eh poised anaerobic medium. Superficial scraping is done with a dull edged means, such as for example a dull edged scalpel blade. After the scraping, the lumen is washed again followed by scraping with a sharp edged means such as, for example, the sharp edge of a scalpel or other suitable instrument. The sharp edged means and lumen wall are washed with medium, as described above, to obtain epithelial cells and indigenous microflora and the washings are collected in a sterile vessel. The tissue can also be cut directly into the culture medium without first scraping. It is preferable to keep the tissue in a reduced atmosphere, i.e. under a stream of nitrogen when the procedure is initiated. The wash or cuttings, with associated epithelial cells and microflora, are suspended and the contents innoculated into sterile anaerobic medium for culture. As used herein, the term microflora is intended to include indigenous bacteria. The culture is incubated anaerobically at about 35–40° C. for approximately 48 hours, transferred to fresh anaerobic medium and reincubated for approximately 48 more hours. This second incubation is the second 48 hour subculture passage and is the most preferred LMCES preparation used. Other subculture passages can also be used as described above. The culture is then assayed for the presence of human enteropathogens using any appropriate and conventional isolation techniques. Cultures, free of pathogens, are administered immediately, freeze-dried or frozen using conventional techniques for freezing cultured cells. Blood from donor animals should be serologically tested for antibody levels to pertinent host animal, including human, pathogens. Only cultures from animals not seroconverting should be used.

The following examples are intended only to further illustrate the invention and are not intended to limit the scope of the invention as defined by the claims.

EXAMPLE 1

Preparation of Bovine Livestock Mucosal CE Cultures

The intestines of a healthy adult bovine are obtained at a local slaughter establishment and transported in a plastic bag to the laboratory within one hour in a sterile anaerobic environment. The mucosal culture is prepared from the lower intestinal tract. Prior to removal of the piece of intestine to be used, the surrounding area is tied off with string to prevent leakage of intestinal contents. An approximately 4 to 5 inch length is aseptically removed and placed in a sterile container. The container is then placed into a tub which is continuously being flushed with oxygen-free nitrogen gas. All manipulations are done below the rim of the tub to keep the culture to be harvested in an anaerobic environment. The length of the intestinal tissue is carefully inverted on a sterile glass rod without touching the inside surface. Once inverted the contents are removed by a combination of washing and scraping. Washing is done by syringe application of pre-reduced brain heart infusion broth (PR-BHIB).

Any other appropriate anaerobic medium is useable for the washing step. Scraping is done with the dull edge of a sterile scalpel blade. The lumen is washed, scraped and then washed again. At this point the cecal epithelium is gently scraped off with the sharp edge of the scalpel in a scraping is preferred. However, the tissue could be cut directly into the culture medium. After scraping of the inverted intestine, the scalpel and lumen wall tip are washed again with PR-BHIB. This final wash is collected in a sterile vessel. The wash, with associated epithelial and bacterial cells, is aspirated with a sterile syringe and needle, and used to inoculate into a tube of sterile PR-BHIB through a rubber septum. These tubes are incubated at 35° C. for 48 hours, transferred and re-incubated for a second 48 hours. The culture is examined for the presence of human enteropathogens of interest such as Salmonella, $E.$ $coli$ and Campylobacter species. If the culture is free of both human and animal pathogens and deemed safe, it is now ready for application or storage for later use.

EXAMPLE 2

Test of Bovine LMCES Efficacy

Bovine LMCES compositions, as described above in Example 1, are administered to new born calves about two times within approximately the first 24 hours of life. The culture is given orally by use of a bottle and nipple. Each treated calf receives about 500 ml of the LMCES, undiluted or up to about 10 timed diluted in milk at each application. After administration, the calves are allowed to feed as usual. About twenty four hours after administration, each calf is given about $10^8$ cells of a nalidixic acid resistant $E.$ $coli$ 0157:H7 by oral gavage. Following challenge the calves are grown in isolation chambers for about seven days to allow any transient $E.$ $coli$ 0157:H7 cells to clear the intestinal tract. The calves are then sacrificed, the ceca aseptically removed and placed into sterile plastic bags. The ceca are then assayed for presence and level of $E.$ $coli$ 0157:H7. The mean log number of the target pathogen per grain of ceca for the entire group is called the colonization factor (CF). The ratio of the CF (untreated control/CF (Treatment group)) is called the protection factor (PF). By comparing the PF of one mucosal CE culture to the PF of another culture, a relative value for degree of protection is obtained for the culture.

EXAMPLE 3

Preparation of Porcine Mucosal CE Cultures

A healthy, approximately 1 to 6 months of age to fully mature, juvenile hog is tranquilized with a cocktail of drugs as is routinely used in the art. A mixture of 8 mg/kg Ketaset, 6 mg/kg Telazol and 4 mg/kg Rompun was used. The hog is then sacrificed by bleed out. One cecum is aseptically removed and placed in a sterile petri dish. The dish is then placed into a tub which is continuously being flushed with oxygen-free nitrogen gas. All manipulations must be done below the rim of the tub to keep the culture to be harvested in an anaerobic environment. The length of the cecum is carefully inverted on a sterile implement without touching the inside surface. Once inverted, the contents are removed by a combination of washings and scraping. Washing is done by syringe application of pre-reduced broth. Scraping is done with the dull edge of a sterile instrument. The lumen is washed, scraped, and then washed again. At this point the cecal epithelium is gently scraped with the sharp edge of a scalpel or may be cut in small sections (about 5 cm). After scraping of the inverted cecum, the scalpel and lumen wall tip are washed again with PR-BHIB. This final wash or cecal sections is/are collected in a sterile vessel. The wash, with associated bacterial cells, is aspirated with a sterile syringe and needle, and used to inoculate into a tube of sterile PR-BHIB through a rubber septum. These tubes are incubated at approximately 35° C. for approximately 48 hours, transferred and reincubated for an approximately second 48 hours. The culture is examined for the presence of human enteropathogens of interest such as Salmonella, E. coli, and Campylobacter species. If the cultures is free of pathogens and deemed safe, it is ready for application or storage.

EXAMPLE 4

Test of Porcine Livestock Mucosal CE Culture (LMCES) Efficacy

Sows with known farrowing dates were kept in farrowing crates in isolation units. Each sow was checked every four hours beginning one day before the known farrowing date to ensure that the first LMCES culture was administered in a timely manner. At farrowing, pigs were allowed to suckle to insure that they obtained colostrum and each pig was given approximately 5 ml of LMCES by oral gavage between about 2 and 6 hours post-farrowing. A second dose of approximately 5 ml was administered at about 24 hours. Pigs were challenged with about $10^3$ CFU S. choleraesuis by intranasal instillation about 48 hours post-farrowing (24 hours past the last LMCES administration). After the preparation is administered, the pigs are allowed to feed as usual. Rectal temperatures and rectal swabs were taken daily for about 7 days post-challenge from each pig and cultured for Salmonella. At about day 7 postchallenge, all pigs were sacrificed and necropsied. Tissues were collected for qualitative bacteriology and included tonsil (ton), mandibular lymph node (mln), lung, brachiale lymph node (bln), liver, spleen (spl), middle ileum, ileocolic junction (icj), ileocolic lymph nodes, cecum (cec), cecal contents (cc), colon (col), colonic lymph nodes, and stomach wall (sw). Quantitative bacteriology was also conducted on the cecal contents and ileocolic junction to determine the level of Salmonella within tissues.

In order to assess the impact the sows may have had on the pigs, sow feces was also collected and cultured prior to farrowing, within about 48 hours after farrowing and at about day 7 post-challenge of the pigs (sows were never directly challenged with S. choleraesuis). Control pigs were not given LMCES but were challenged at about 48 hours of age. Tissues were collected and processed as described above.

Clinical signs were inapparent in all pigs throughout the experiment. Recovery of Salmonella from rectal swabs was variable. However, about 41% of the tissues were positive from the LMCES treated pigs versus about 63% positive tissues from the control pigs (Table 1, Summary for Trials 1 and 2). From pigs originating from negative sows (Trial 1—sows 1,2,3 and Trial 2—sow 2) 39% [120/310] of the tissues were positive versus 78% [47/60] (Trial 1—control sow negative) positive tissue from the control sow. Salmonella reduction is imparted in CE treated versus untreated pigs. An about 2 to 5 log reduction of Salmonella in the cecal contents (CC) or ileocolic junction (ICJ) was observed in the LMCES treated pigs when compared to the controls (Salmonella was cleared from the ICJ and CC in pigs from 2 and 1 sows, respectively) (Table 2, Trials 1 and 2). In trial 1, all sows were pathogen-free. All sows were originally shedding one serogroup then stopped prior to farrowing. At farrowing, sow 1 and the control sow were shedding serogroup B. In trial 2, pigs from sow 1 and 2 were shedding only B type Salmonella and not the challenge S. choleraesuis. Controls for trails 1 and 2 did not receive any LMCES, only the challenge organism. As can be seen, there is not only reduced levels of the challenge organism but also reduced levels of the native colonization. While reduction is observed in pigs already colonized with Salmonella other than that received from the challenge, the degree of protection is reduced suggesting that in suckling pigs, an earlier administration may be warranted.

The foregoing detailed description is for the purpose of illustration. Such detail is solely for that purpose and those skilled in the art can make variations therein without departing from the spirit and scope of the invention.

TABLE ONE

Incidence and Levels of Salmonella in Pigs Provided LMCE Treatment or Not Provided (Ctrl) Treatment

SUMMARY

| | Swabs | % POS | TISSUES | % POS | Log10/g CC | ICJ |
|---|---|---|---|---|---|---|
| CE | 57/281 | 20.3 | 157/380 | 41.3 | 3.19 | 3.13 |
| Ctrl | 72/114 | 63.2 | 95/150 | 63.3 | 5.09 | 5.45 |

TABLE TWO

Incidence and Levels of Salmonella 2--days after Challenge in Pigs Provided LMCE Treatment or Not Provided (Ctrl) Treatment Trial 1:

| SOW/ NO.Pigs | Pass. No. | NO.POS. Swabs | No.POS. Tissues | % POS. Tissues | log10 CC | log10 ICJ |
|---|---|---|---|---|---|---|
| 1-/½/2 | 0 | 36/40 | 90 | | 3.86 | 3.65 |
| 2-/½/2 | 1 | 21/60 | 35 | | 2.51 | 3.35 |
| 3-/12 | 4/5 | 2 | 43/120 | 36 | 1.5 | 0 |
| SUM | | Ns | 100/220 | 45 | 3.16 | 3.14 |
| CONTROL | C/6 | 0 | 47/60 | 79 | 5.39 | 5.74 |

All sows negative

| Tissues | ton | bln | lung | liver | spl | col | icj | cec | cc | sw |
|---|---|---|---|---|---|---|---|---|---|---|
| 1(4) | 3 | 4 | 4 | 3 | 4 | 4 | 4 | 3 | 4 | 3 |
| 2(6) | 0 | 3 | 3 | 3 | 3 | 0 | 4 | 2 | 2 | 1 |
| 3(12) | 2 | 12 | 9 | 7 | 6 | 0 | 3 | 1 | 3 | 0 |
| c (6) | 4 | 4 | 5 | 5 | 5 | 5 | 5 | 5 | 5 | 4 |

Trial 2:
All salmonellae

| Sow/ No.Pigs | Pass.No. | No. Pos. Swabs | No. Pos, Tissues | % Pos. Tissues | log10 CC | log10 ICJ |
|---|---|---|---|---|---|---|
| ]+/7 | 4/4 | 50/56* | 37/70 | 53 | 2.32 | 1.38 |
| 2-/9 | 6/7 | 4/49* | 20/90 | 22 | -0- | -0- |
| SUM | | na | 57/160 | 36 | 2.02 | 1.08 |
| C+/9 | | 72/72* | 48/90 | 53 | 3.33 | 4.23 |

*shedding only B

| Tissues | ton | bln | lung | liver | spl | col | icj | cec | cc | sw |
|---|---|---|---|---|---|---|---|---|---|---|
| 1(7) | 2 | 6 | 6 | 5 | 4 | 4 | 4 | 2 | 4 | o |
| 2(9) | 1 | 5 | 3 | 2 | 3 | 1 | 1 | 2 | 2 | 0 |
| c | 2 | 3 | 3 | 3 | 2 | 6 | 9 | 9 | 9 | 2 |

C1 Only:

| SOW/ NO.Pigs | Pass. No. | NO.POS. Swabs | No.POS. Tissues | % POS. Tissues | log10 CC | log10 ICJ |
|---|---|---|---|---|---|---|
| 1+/7 | 4/4 | na | 19/70 | 27 | -0- | -0- |
| 2-/9 | 6/7 | na | 18/90 | 20 | -0- | -0- |
| SUM | | na | 37/160 | 23 | -0- | -0- |
| C+/9 | | na | 16/98 | 18 | 2.98 | 4.23 |

| Tissues | ton | bln | lung | liver | spl | col | icj | cec | cc | sw |
|---|---|---|---|---|---|---|---|---|---|---|
| 1(7) | 1 | 5 | 5 | 4 | 4 | 0 | 0 | 0 | 0 | 0 |
| 2(9) | 1 | 5 | 3 | 2 | 3 | 1 | 1 | 1 | 1 | 0 |
| C | 1 | 3 | 3 | 2 | 2 | 1 | 1 | 1 | 1 | 1 |

We claim:

1. An isolated pathogen-free animal mucosal-derived composition comprising a pathogen-free livestock competitive exclusion subculture obtained from a pathogen-free animal.

2. The composition of claim 1 wherein said subculture is an anaerobic subculture.

3. The composition of claim 1 wherein said culture is obtained from scrapings of intestinal tracts of said pathogen-free livestock.

4. The composition of claim 3 wherein said intestinal track is the lower intestine.

5. The composition of claim 1 wherein said composition is prepared by aseptically removing lower intestine from said pathogen-free animal, inverting said intestine, washing said inverted intestine, scraping said inverted intestine, repeating said washing and scraping steps to obtain epithelial cells and microflora, inoculating said washings and scrapings into sterile anaerobic medium to form an inoculum, culturing said inoculum for 48 hours to form a culture, and subculturing said culture to obtain said composition.

6. An isolated pathogen-free livestock intestinal mucosal composition collected from pathogen-free animals having the property of reducing colonization of enteropathogenic bacterial in intestinal tracts of animals wherein said pathogen-free composition is prepared by aseptically removing lower intestine from said pathogen-free animal, inverting said intestine, washing said inverted intestine, scraping said inverted intestine, repeating said washing and scraping steps to obtain epithelial cells and microfloria, inoculating said washings and scrapings into sterile anaerobic medium to form an inoculum, culturing said inoculum for 48 hours to form a pathogen-free culture, and subculturing said culture to obtain said pathogen-free culture.

* * * * *